(12) United States Patent
Singh

(10) Patent No.: US 8,734,013 B2
(45) Date of Patent: May 27, 2014

(54) SMALL MOBILE X-RAY SCANNING SYSTEM

(76) Inventor: Satpal Singh, Potomac, MD (US)

( * ) Notice: Subject to any disclaimer, the term of this patent is extended or adjusted under 35 U.S.C. 154(b) by 436 days.

(21) Appl. No.: 13/080,547

(22) Filed: Apr. 5, 2011

(65) Prior Publication Data

US 2012/0257717 A1 Oct. 11, 2012

(51) Int. Cl.
*H05G 1/02* (2006.01)
*H05G 1/60* (2006.01)

(52) U.S. Cl.
CPC ... *H05G 1/02* (2013.01); *H05G 1/60* (2013.01)
USPC .......................... 378/197; 378/146; 378/198

(58) Field of Classification Search
CPC .................................. H05G 1/02; H05G 1/60
USPC .................. 378/146, 189, 190, 192, 196–198
See application file for complete search history.

(56) References Cited

U.S. PATENT DOCUMENTS

| | | | | | |
|---|---|---|---|---|---|
| 3,617,749 | A | * | 11/1971 | Massiot | 378/181 |
| 4,775,994 | A | * | 10/1988 | Kranvogel | 378/197 |
| 5,835,558 | A | * | 11/1998 | Maschke | 378/198 |
| 7,500,784 | B2 | * | 3/2009 | Grebner et al. | 378/198 |
| 7,695,192 | B2 | * | 4/2010 | Henderson et al. | 378/198 |
| 7,810,994 | B2 | * | 10/2010 | Ohmura et al. | 378/196 |
| 2003/0099328 | A1 | * | 5/2003 | Jensen et al. | 378/198 |
| 2008/0075232 | A1 | * | 3/2008 | Agrawal et al. | 378/198 |
| 2010/0189226 | A1 | * | 7/2010 | Kotowski et al. | 378/198 |

* cited by examiner

*Primary Examiner* — Thomas R Artman

(57) ABSTRACT

This invention describes a method of inspecting unidentified packages placed on the floor or ground, or on desktops or counters. The method uses a transmissive x-ray system mounted on a small mobile platform such as robots. X-ray is emitted from the source directed away from the platform and detected by a detector arm supported on an extended member attached to a vertical member such that the object to be inspected can pass in between the detector arm and the x-ray source. To scan portions of the object close to the ground, the height of the x-ray source is lowered close to the ground, and during transportation, it is raised up so that there is more clearance from the ground. To scan objects located on higher levels such as desks, the detector arm has an angular movement greater than ninety degrees with respect to an axis that has a vertical component.

12 Claims, 3 Drawing Sheets

SMALL MOBILE X-RAY SCANNING SYSTEM

BACKGROUND OF THE INVENTION

1. Field of the Invention

This invention describes a novel method of inspecting unidentified packages placed on the floor or ground, or on desktops or counters. The method uses a transmissive x-ray system mounted on a small mobile platform such as robots.

2. Description of the Related Art

Majority of x-ray systems in use today are fixed or stationary systems like the ones seen at airports for scanning bags. If an unidentified bag or object is found on the lobby of an airport, to examine it, the object or the bag has to be picked up and placed on the belt of a the stationary x-ray system. This not only puts the risk of the bomb squad members handling the object at risk, but any movement of the bag can trigger an explosion causing serious fatalities and damages.

An alternative approach used is to use small hand held x-ray sources which are hand carried by a member of the bomb squad and placed in close proximity of the unidentified bag. On the other side of the bag is then placed a film or detector panel which is sensitive to x-rays and can record an image of the object when x-rays pass through it. The problem with this approach is that the hand held x-ray sources are pulsed, hence their flux is low which results in a low signal to noise ratio and hence a low quality image unless long exposure times are used. A greater problem with such sources is that the high voltage required to generate the x-rays is generated by using some sort of a spark technology that produces a flash of an x-ray, producing x-rays in such a fashion does not facilitate itself to controlling reasonably well enough the amplitude of the high voltage and hence the energy of the x-ray. If one is able to better control the x-ray energy, one can scan the object with different energies and select an image that is best created by an optimal energy level for that particular object. For example, when scanning soft or low density objects, one would like to set the energy level low, using higher energy, would give a washed out effect on the scanned image. Further using different energy levels, one can make a determination of atomic number and density and make more accurate prediction if the contents of the bag or object are explosive in nature or not.

In addition to not being able to set the energy accurately enough, there is a huge risk to human personnel who hand carry the x-ray source and the film or detector panel and place them close to the suspected object or bag.

If an object or bag is left on a desk top, there might not be enough room on the desk top to place the hand held x-ray source on one side and the detector on the other side of the bag.

Other scanning systems include mobile systems that are large and mounted on a truck, these are not suitable for imaging small objects. Such systems can not produce images of those portions of the object that are close to the ground because the x-ray source is located at a much higher level. This is important as explosives might be located on the lower portions of the bag or object.

Accordingly, the objects of this invention are to overcome the above limitations as stated next.

OBJECTS OF THE INVENTION

It is, accordingly, an object of the invention is to greatly reduces the risk to human lives of the bomb squad members by providing a small mobile x-ray scanning system that is mounted on a robotic platform.

It is also an objective of the invention to be able to generate scanned images of those portions of the objects that are close to the ground.

An additional objective is to use a non pulsed x-ray source that can generate high flux or intensity x-rays which are needed to generate higher quality x-ray images. Additional objective is to be able to set the energy of the x-rays so that the object can be scanned with different energies and a determination can be made if the contents of the object are explosive or not.

It is also an objective of the invention to be able to scan objects located on desk or counter tops using a small robot that is moving at a lower level closer to the floor.

These and other objects will become apparent in the description that follows.

SUMMARY OF THE INVENTION

The x-ray scanning system in accordance with this invention is implemented by installing a x-ray source on a small mobile platform which emits a radiation beam outwards and away from the platform. This radiation passes through the object to be inspected and is detected by a detector arm that is suspended like a boom from a vertical member attached to the mobile platform. One important aspect of the invention is that the radiation source is lowered towards the floor when scanning objects placed on the floor. In the preferred embodiment of the invention, the detector arm is comprised of two arms or segments which have an angular motion with respect to each other and to an axis that has a vertical component. When scanning objects located at higher levels such as on top of table or desktops or counters, the angle of the detector arm with respect to the vertical axis is set to non ninety degrees, so that the detector arm is pointing upwards.

DETAILED DESCRIPTION OF THE PREFERRED EMBODIMENTS

Figure 1:
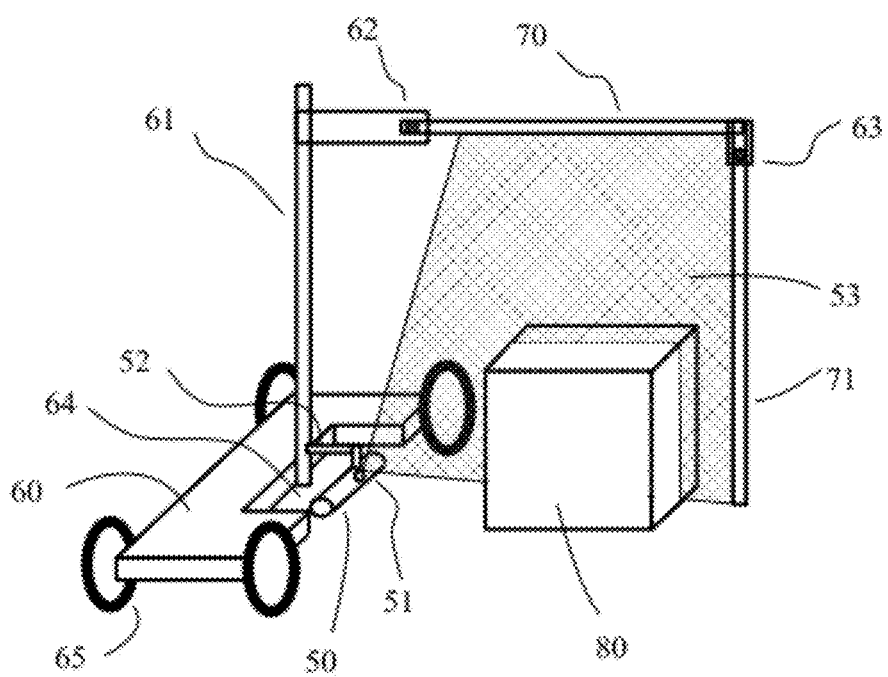
FIG. 1 shows a simplified schematic of a preferred embodiment of this invention.

In describing the preferred embodiment and its alternatives, specific terminology will be used for the sake of clarity. However, the invention is not limited to the specific terms so used, and it should be understood that each specific term includes all its technical equivalents which operate in a similar manner to accomplish similar purpose.

The accompanying figures show a preferred embodiment of the present invention. For the sake of clarity in the drawings, the ordinary details relating to the mechanics and electronics of the system have been omitted as these are well known to a person skilled in the field.

As shown in FIG. 1, the scanning method employs using a robotic or a small mobile or a portable platform 60 that carries a x-ray or a radiation source 50 with a focal point 51 from where emits a radiation beam 53. Not shown to avoid clutter in the drawing are ordinary details like the collimator to shape the radiation beam, the high voltage electronics required to generate x-rays, the motors to drive the platform, and other mechanical and electrical details that are well known to a person skilled in the art. The x-ray source 50 is attached by a mechanical means 52 to a vertical member 61. The mechanical means 52 can be raised or lowered and attached at different heights to 61 thereby allowing to adjust the height of x-ray source 50. The diameter of the wheels 65 and the height of the platform 60 is designed to be high enough so that the platform can clear ordinary obstacles in the path. The platform 60 has a cut out 64 through which the x-ray source 50 can be lowered as shown in FIG. 1.

Figure 2:
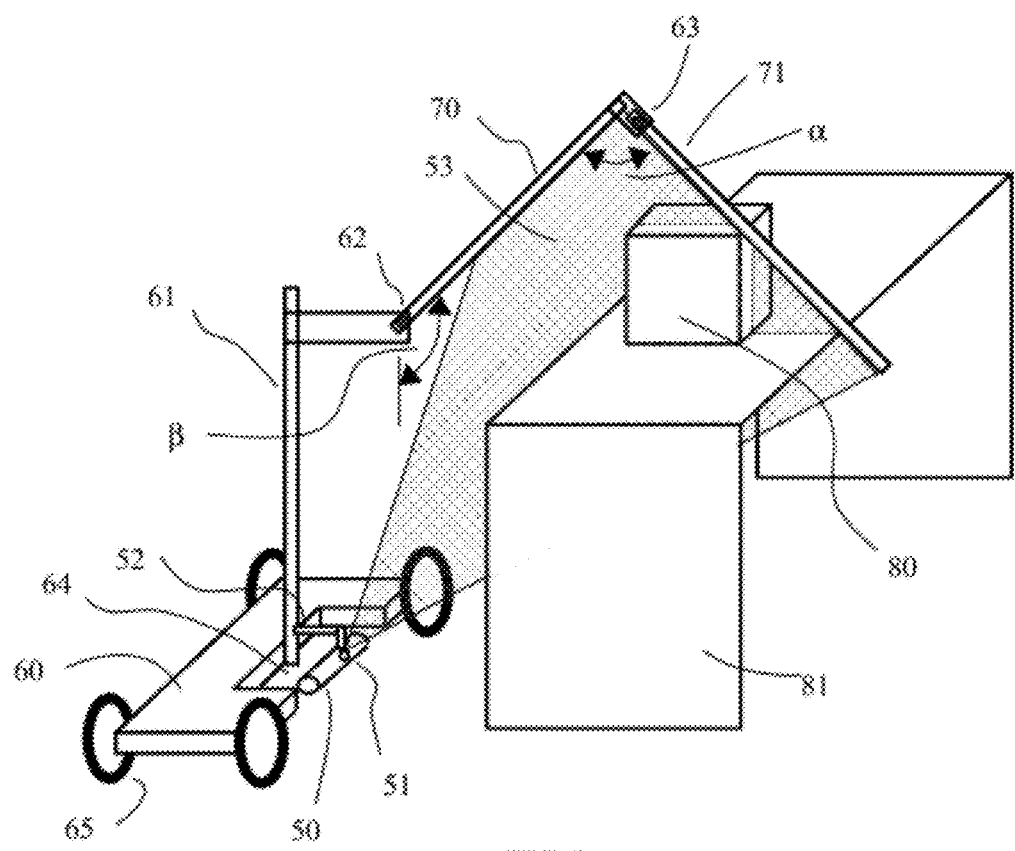
FIG. 2 shows further illustrates the use of the system.
Figure 3:
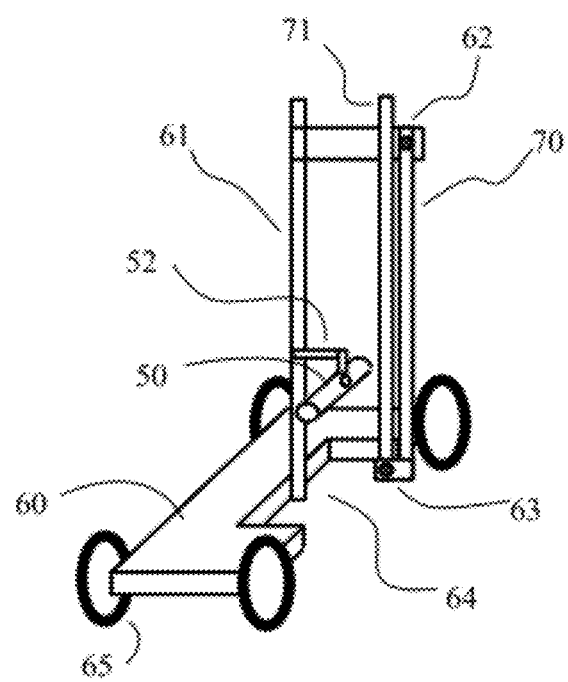
FIG. 3 shows the stowed away position of the system.

The vertical member 61 supports a detector arm comprising of segments 70 and 71. The detector segment 70 is shown horizontal in FIG. 1, but is pivoted at 62 and can have an angular motion and can be positioned at different angles $\beta$ with respect to a vertical axis that is parallel to the vertical member 61 as shown in FIG. 2 and FIG. 3. Likewise the detector segment 71 is pivoted at 63 and can make an adjustable angle $\alpha$ with respect to member 70 as shown in FIG. 2 and FIG. 3. It should be noted that both angles $\alpha$ and $\beta$ are zero in FIG. 3. Not shown to avoid clutter in the drawings are ordinary details like the actuators to change the angle of the arms or the segments 70 and 71, but these are well known to a person skilled in the art.

FIG. 1 shows the object 80 to be scanned to be placed at ground level. According to the method of this invention, the x-ray source 50 is first lowered closer to the ground through the cutout 64 so that the portion of the object touching and just above the ground can also be imaged. The mobile platform 60 is then moved so that the detector comprising of 70 and 71 sweeps over the object to affect a scan in order to image it and inspect it.

FIG. 2 shows the object 80 located at a much higher level on top of a desk 81. In order to scan an objected located at such a height, the angles $\beta$ and $\alpha$ of the detector arms 70 and 71 are adjusted as shown in FIG. 2 such that the radiation beam 53 intercepts the object. It should be noted by changing the angles $\alpha$ and $\beta$, the angle of the detector arm comprising of 70 and 71 is changed with respect to axis that is vertical. It should be noted that the angles $\alpha$ and $\beta$ can be with respect to axes that are not vertical but slanted with vertical components, for example the vertical member 61 need not be vertical but at forty five degrees to the vertical.

FIG. 3 shows the stow away position of the system. It is important to note that the height of x-ray source 50 has been raised by raising the mechanical means 52 and attaching it at a higher height onto the vertical member 61 as shown in FIG. 3. This facilitates the transport of the platform 60 over higher obstacles. However, at the time of imaging or scanning, the height of the source 50 is lowered closer to the ground as shown in FIG. 1. A lower height of x-ray source 50 is desired when scanning as it allows to scan the lower portions of the object 80 that are closer to the ground.

In FIG. 1 and FIG. 2, the detector arm has been shown to be perpendicular to or at ninety degrees to the length of the mobile platform, however the detector arm could be at any other angle which would yield x-ray images at different angles thereby allowing one to obtain multiple views of the object. The multiple views from different angles could then be combined in software to build a 3D information of the object.

In another embodiment of the invention, the x-ray source 50 is lowered to the ground through the cutout 64 in the platform 60. The mobile platform is kept stationary and the only the detector arm in FIG. 1 or FIG. 2 is swept in an arc that changes the angle that the detector arm makes to a horizontal line or axis that is parallel to the length of the platform 60. It should be noted that this horizontal line or axis need not be horizontal but could be pointing up or down with a horizontal component.

There are several embodiments to the invention. It should be noted that the important aspects of the invention are a means to be able to lower the height of radiation source during scan, and that the detector arms 70 and 71 can make angles $\beta$ and $\alpha$ that are greater or less than ninety degrees whereas in the case of other mobile systems that are mounted on trucks or vans, the angle when scanning is approximately ninety degrees.

In the illustrations shown in FIG. 1 and FIG. 2, the radiation beam 53 has been shown to be fan beam shaped, however it can be conical.

In an alternate form of embodiment, the radiation source 50 could be any radiation source other than x-rays.

In other alternate forms of embodiments, there can be more than two detector segments 70 and 71, or it could be just one detector arm 70 that extends out long enough to catch all the radiation beam passing through the object 80 in FIG. 1, or there could be one detector arm that is curved like a semicircle.

It should be noted that multiple views can be obtained by positioning the source 50 at different heights, and also by positioning the platform 60 at different angles with respect to the object 80.

These multiple views can then be analyzed by a computing means to determine the 3D structure or composition of the object 80 being scanned.

The foregoing description of the invention and its embodiments should be considered as illustrative only of the concept and principles of the invention. The invention may be configured in a variety of ways, shapes and sizes and is not limited to the description above. Numerous applications of the present invention will readily occur to those skilled in the art. Therefore, it is desired that the scope of the present invention not be limited by the description above but by the claims presented herein.

The invention claimed is:

1. A portable device especially suited to inspect an object at a height close to ground level comprising of:
    a radiation source emitting a radiation beam;
    a means to adjust the height of said radiation source wherein said means to adjust the height is configured to lower said radiation source sufficiently close to ground so that lowest parts of said object are illuminated by said radiation beam;
    a detector arm supporting detectors to detect said radiation beam;
    a means to position said detector arm at a sufficient distance to allow said object to be inspected to be positioned in between said radiation source and said detector arm;
    a means to change the angle of said detector arm with respect to an axis that has a vertical component;
    a means to change the relative position of said detector arm to said object; and
    a computing means to analyze the data from said detectors.

2. A device of claim 1 further comprising of:
    a means to change the angle of said detector arm with respect to an axis that has a horizontal component.

3. A device of claim 2 wherein said detector arm further comprises of:
    two or more detector segments.

4. A device of claim 1 wherein said detector arm further comprises of:
    two or more detector segments.

5. A method especially suited to inspect an object at a height close to ground level comprising the steps of:
    using a radiation source emitting a radiation beam;
    using a means to adjust the height of said radiation source wherein said means to adjust the height is configured to lower said radiation source sufficiently close to ground so that lowest parts of said object are illuminated by said radiation beam;

using a detector arm supporting detectors to detect said radiation beam;

positioning said detector arm at a sufficient distance to allow said object to be inspected to be positioned in between said radiation source and said detector arm;

changing the angle of said detector arm with respect to an axis that has a vertical component;

scanning said object by moving said detector arm relative to said object; and using a computing means to analyze the data from said detectors.

6. A method of claim 5 further comprising the step of:

changing the angle of said detector arm with respect to an axis that has a horizontal component.

7. A method of claim 6 wherein the step of positioning said detector arm further comprises of:

positioning two or more detector segments on said detector arm.

8. A method of claim 7 further comprising the steps of:

scanning said object from different angles to obtain multiple views; and analyzing said multiple views to make a determination of the nature or composition of said object.

9. A method of claim 6 further comprising the steps of:

scanning said object from different angles to obtain multiple views; and analyzing said multiple views to make a determination of the nature or composition of said object.

10. A method of claim 5 wherein the step of positioning said detector arm further comprises of:

positioning two or more detector segments on said detector arm.

11. A method of claim 10 further comprising the steps of:

scanning said object from different angles to obtain multiple views; and analyzing said multiple views to make a determination of the nature or composition of said object.

12. A method of claim 5 further comprising the steps of:

scanning said object from different angles to obtain multiple views; and analyzing said multiple views to make a determination of the nature or composition of said object.

\* \* \* \* \*